(12) United States Patent
Pasha

(10) Patent No.: US 12,133,690 B2
(45) Date of Patent: Nov. 5, 2024

(54) SYSTEMS AND METHODS FOR MATCHING IMAGES OF THE SPINE IN A VARIETY OF POSTURES

(71) Applicant: Medtronic Navigation, Inc., Louisville, CO (US)

(72) Inventor: Saba Pasha, Houston, TX (US)

(73) Assignee: Medtronic Navigation, Inc., Louisville, CO (US)

( * ) Notice: Subject to any disclaimer, the term of this patent is extended or adjusted under 35 U.S.C. 154(b) by 17 days.

(21) Appl. No.: 17/497,586

(22) Filed: Oct. 8, 2021

(65) Prior Publication Data
US 2023/0115512 A1 Apr. 13, 2023

(51) Int. Cl.
*A61B 34/10* (2016.01)
*G06T 7/00* (2017.01)
*G06T 17/00* (2006.01)

(52) U.S. Cl.
CPC ............ *A61B 34/10* (2016.02); *G06T 7/0016* (2013.01); *G06T 17/00* (2013.01); *A61B 2034/105* (2016.02); *G06T 2207/20224* (2013.01); *G06T 2207/30004* (2013.01); *G06T 2210/41* (2013.01)

(58) Field of Classification Search
CPC ........ A61B 2034/102; A61B 2034/105; A61B 2034/107; A61B 2034/2051; A61B 2034/2072; A61B 2034/252; A61B 2034/254; A61B 2034/256; A61B 2090/365; A61B 34/10; A61B 34/20; A61B 34/25; G16H 20/40; G16H 30/20; G16H 50/50
See application file for complete search history.

(56) References Cited

U.S. PATENT DOCUMENTS

| | | | |
|---|---|---|---|
| 11,439,514 B2 * | 9/2022 | Casey | A61B 17/7035 |
| 12,004,988 B2 * | 6/2024 | Ontiki | A61B 5/4561 |
| 2004/0171924 A1 * | 9/2004 | Mire | A61B 34/20 |
| | | | 600/407 |

(Continued)

FOREIGN PATENT DOCUMENTS

| | | | | |
|---|---|---|---|---|
| WO | WO-2020216934 A1 * | 10/2020 | | A61B 34/10 |
| WO | WO 2021/061924 | 4/2021 | | |

OTHER PUBLICATIONS

Ji et al. "Intraoperative CT as a registration benchmark for Intervertebral motion compensation in image-guided open spinal surgery," International Journal of Computer Assisted Radiology and Surgery, Jul. 2015, vol. 10, No. 12, pp. 2009-2020.

(Continued)

*Primary Examiner* — Ming Wu
(74) *Attorney, Agent, or Firm* — Sheridan Ross P.C.

(57) ABSTRACT

A system or method according to at least one embodiment of the present disclosure includes receiving a preoperative image of a patient in a first posture; receiving an intraoperative image of the patient in a second posture; comparing the preoperative image of the patient in the first posture with the intraoperative image of the patient in the second posture; and determining, based on comparing the preoperative image of the patient in the first posture with the intraoperative image of the patient in the second posture, a difference between the first posture and the second posture, the adequate surgical changes are imparted to the second posture to achieve satisfactory surgical outcome.

18 Claims, 5 Drawing Sheets

(56) References Cited

U.S. PATENT DOCUMENTS

| | | | |
|---|---|---|---|
| 2006/0002630 A1 | 1/2006 | Fu et al. | |
| 2006/0241388 A1* | 10/2006 | Lavallee | A61B 34/20 |
| | | | 600/416 |
| 2020/0015911 A1 | 1/2020 | Yi | |
| 2020/0078097 A1 | 3/2020 | Gregerson et al. | |
| 2020/0360089 A1 | 11/2020 | Lee et al. | |
| 2021/0153808 A1* | 5/2021 | Tada | G16H 50/20 |

OTHER PUBLICATIONS

International Search Report and Written Opinion for International (PCT) Patent Application No. PCT/IB2022/058970, dated Jan. 30, 2023, 16 pages.

* cited by examiner

SYSTEMS AND METHODS FOR MATCHING IMAGES OF THE SPINE IN A VARIETY OF POSTURES

FIELD

The present technology generally relates to surgical imaging and relates more particularly to matching medical images in various postures.

BACKGROUND

Surgical robots may assist a surgeon or other medical provider in carrying out a surgical procedure or may complete one or more surgical procedures autonomously. Intraoperative surgical images may be captured during a surgery. Intraoperative images may show patient anatomy.

SUMMARY

Example aspects of the present disclosure include:

A method according to at least one embodiment of the present disclosure comprises: receiving a preoperative image of a patient in a first posture; receiving an intraoperative image of the patient in a second posture; comparing the preoperative image of the patient in the first posture with the intraoperative image of the patient in the second posture; and determining, based on comparing the preoperative image of the patient in the first posture with the intraoperative image of the patient in the second posture, a difference between the first posture and the second posture.

Any of the aspects herein, further comprising: providing an indication of the difference and a suggested motion for the patient to reduce the difference; receiving an additional intraoperative image of the patient, wherein the additional intraoperative image of the patient is received after the patient is moved from the second posture to a third posture; comparing the preoperative image of the patient in the first posture with the additional intraoperative image of the patient in the third posture; and determining, based on comparing the preoperative image of the patient in the first posture with the additional intraoperative image of the patient in the third posture, a difference between the first posture and the third posture.

Any of the aspects herein, wherein the preoperative image of the patient in the first posture comprises a two-dimensional (2D) image, and wherein the method further comprises: generating, with the 2D image, a three-dimensional (3D) model of an anatomical element of the patient; and comparing the 3D model of the anatomical element of the patient with a view of the anatomical element in the intraoperative image.

Any of the aspects herein, further comprising: determining, based on the difference between the first posture and the second posture, an alignment of a first segment of a spine of the patient with a second segment of the spine of the patient.

Any of the aspects herein, wherein the first segment of the spine is surgically manipulated, and wherein the second segment of the spine not surgically manipulated.

Any of the aspects herein, further comprising: updating, when the alignment falls below a threshold value, a surgical plan.

Any of the aspects herein, wherein the preoperative image and the intraoperative image are provided as an input to an artificial neural network, and wherein the artificial neural network provides an output that is used to determine the difference between the first posture and the second posture.

Any of the aspects herein, wherein the artificial neural network is trained with a plurality of images from a plurality of different patients, and wherein the output is used to determine a surgical maneuver of a first portion of a spine of the patient to reduce the difference.

Any of the aspects herein, wherein the output of the artificial neural network comprises a confidence score and a suggested intraoperative movement of the patient to reduce the difference between the first posture and the second posture.

Any of the aspects herein, wherein the first segment of the spine is surgically manipulated, and wherein the second segment of the spine is one of not surgically manipulated, fixed, or not altered with a surgical tool or device.

Any of the aspects herein, wherein the preoperative image and the intraoperative image are provided as an input to a model, and wherein the model provides an output that is used to determine the difference between the first posture and the second posture.

Any of the aspects herein, wherein the model is at least one of an artificial neural network, a numerical model, a computational model, or a statistical model, and wherein the model provides an output that is used to determine the difference between the first posture and the second posture.

A system according to at least one embodiment of the present disclosure comprises: a processor; and a memory storing data for processing by the processor that, when processed by the processor, cause the processor to: receive a preoperative image of a patient in a first posture; receive an intraoperative image of the patient in a second posture; compare the preoperative image of the patient in the first posture with the intraoperative image of the patient in the second posture; and determine, based on comparing the preoperative image of the patient in the first posture with the intraoperative image of the patient in the second posture, a difference between the first posture and the second posture.

Any of the aspects herein, wherein the data further cause the processor to: provide an indication of the difference and a suggested motion for the patient to reduce the difference; receive an additional intraoperative image of the patient, wherein the additional intraoperative image of the patient is received after the patient is moved from the second posture to a third posture; compare the preoperative image of the patient in the first posture with the additional intraoperative image of the patient in the third posture; and determine, based on comparing the preoperative image of the patient in the first posture with the additional intraoperative image of the patient in the third posture, a difference between the first posture and the third posture.

Any of the aspects herein, wherein the preoperative image of the patient in the first posture comprises a 2D image, and wherein the data further cause the processor to: generate, based on the 2D image, a 3D model of an anatomical element of the patient; and compare the 3D model of the anatomical element of the patient with a view of the anatomical element in the intraoperative image.

Any of the aspects herein, wherein the data further cause the processor to: render, to a user interface, the 3D model of the anatomical element.

Any of the aspects herein, wherein the first posture comprises the patient in a standing position, and wherein the second posture is different from the first posture.

Any of the aspects herein, wherein the second posture comprises the patient in a non-standing position.

Any of the aspects herein, wherein the data further cause the processor to: cause the preoperative image and the intraoperative image to be provided as an input to an artificial neural network, and wherein the artificial neural network provides an output that is used to determine the difference between the first posture and the second posture.

Any of the aspects herein, wherein the artificial neural network is trained with a plurality of images from a plurality of different patients.

Any of the aspects herein, wherein the output of the artificial neural network comprises a confidence score and a suggested intraoperative movement of the patient to reduce the difference between the first posture and the second posture.

A system according to at least one embodiment of the present disclosure comprises: a processor; and a memory storing data for processing by the processor that, when processed by the processor, cause the processor to: receive a plurality of preoperative 2D images of a patient in a first posture; receive a plurality of intraoperative 2D images of the patient in a second posture different from the first posture; generate, based on the plurality of preoperative 2D images, a first 3D model of an anatomical element of the patient in the first posture; generate, based on the plurality of intraoperative 2D images, a second 3D model of the anatomical element of the patient in the second posture; compare the first 3D model and the second 3D model; and determine, based on the comparison of the first 3D model and the second 3D model, a difference in a first pose of the anatomical element in the first posture and a second pose of the anatomical element in the second posture.

Any of the aspects herein, wherein the data further cause the processor to: render, to a user interface, the first 3D model and the second 3D model.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_0$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
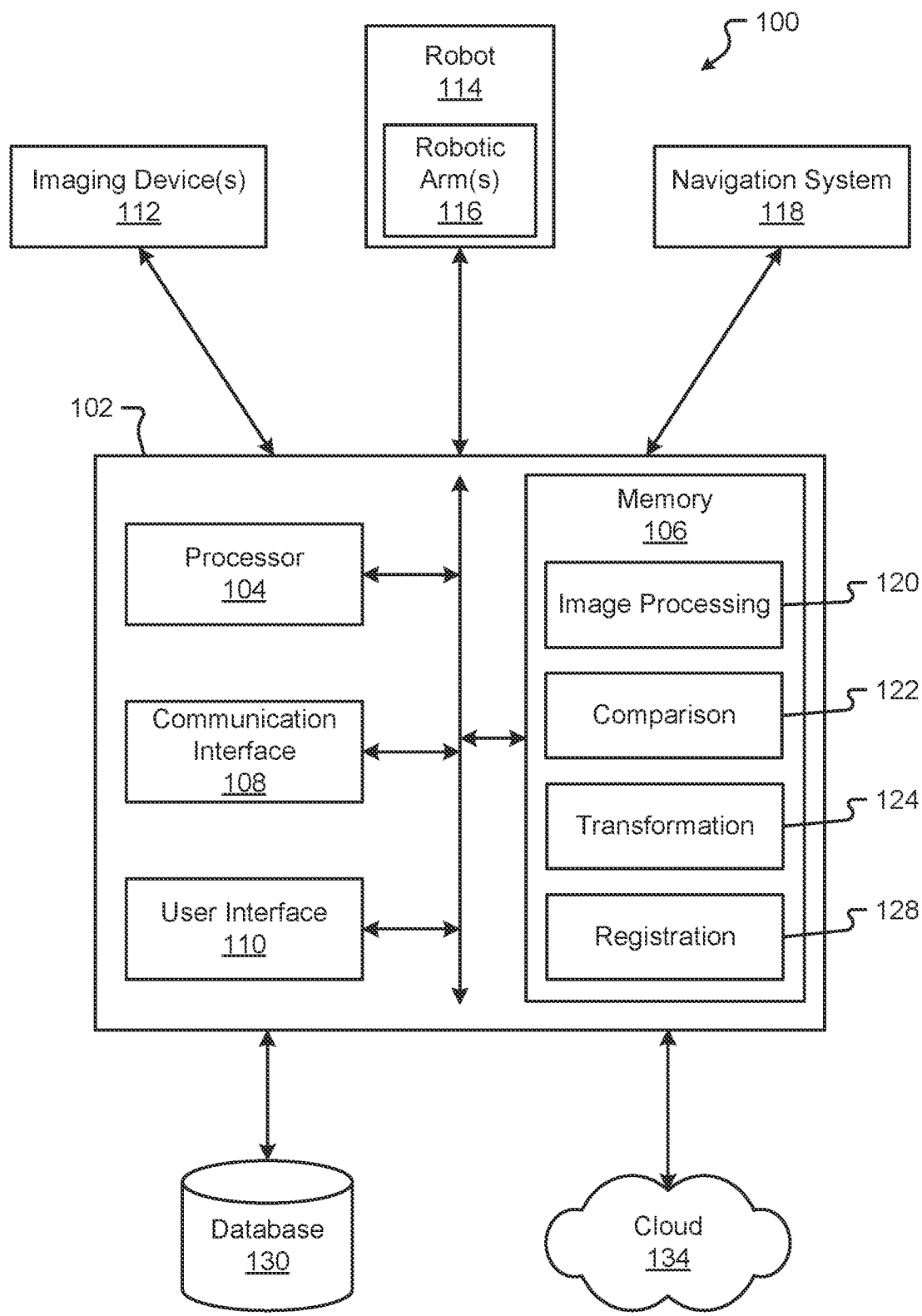
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Surgical planning for a surgery or surgical procedure, such as spinal surgery, may be based on two-dimensional (2D) views of standing images. The spinal surgery may be performed with the patient in the prone, supine, lateral, or decubitus positions, which may impact spinal alignment and may give an unrealistic impression of deformities (e.g., a severity of spine deformity) and/or an unrealistic impression of global spine alignment to the surgeon. Further, a comparison of only 2D images in the two postures (and subsequently planning a surgery based on such a comparison) may be inaccurate, since a deformity of the spine in one plane may be compensated for by spinal realignment in the same or another plane as the posture changes from the standing position to the prone, supine, lateral, or decubitus positions or any other postures at which the patient is positioned intraoperatively. Variation between the patient posture during the surgical and standing postures may result in an intraoperative change in the surgical plan (e.g., the surgeon may have to change or modify the surgical moves and maneuvers during surgery), which may result in an over- or under-correction to account for the deformity or other spinal conditions such as degenerative spine. The correction may result in poor surgical outcomes, patient dissatisfaction of the outcome, and surgeon dissatisfaction with the provided surgical plan.

In accordance with embodiments of the present disclosure, a two-dimensional (2D) or a three dimensional (3D) model of the spine may be provided prior to the surgery and mapped to the 2D or 3D shape of the spine intraoperatively, depending on the spinal condition, a 2D or a 3D model may be deemed more appropriate. For example, for degenerative spine a 2D spinal model may be adequate while a 3D model may be required for deformity, adult scoliosis, pediatric scoliosis etc. As such, the surgeon may be able to better understand the differences between the two postures.

In accordance with embodiments of the present disclosure, artificial intelligence and/or image processing techniques may be used to generate 3D images from preoperative standing images and may match the 3D images to intraoperative 3D images of the spine. By matching the two images, the patient may be prepped for the surgery or surgical procedure in a way that resembles the desired posture or the differences between the two postures can be measured and reported quantitatively. As such, the correction of the spinal condition may be made to match the preoperative surgical plan, which may reduce the need for intraoperative changes to the surgical plan, which may beneficially result in outcomes that more closely match the natural posture of the patient. The relative alignment between the fused and unfused segments of the spine can be visualized intraoperatively to allow the surgeon to modify the spinal alignment intraoperatively and avoid post-operative postural compensatory that may lead to complications. In this embodiment the unfused segment of the spine can be added to the realigned segments of the spine and evaluate the postural outcome of the spinal surgery. In accordance with embodiments of the present disclosure, the methods and systems discussed herein further beneficially enable improved visualization of the postoperative standing posture of the patient resulting from a variety of anatomical elements not impacted by the surgery or surgical procedure (e.g., muscle composition, disc properties, etc.), and/or from postural habits of the patient.

Aspects of the present disclosure include constructing 3D images of a patient spine from calibrated radiographs (i.e., X-rays) during a preoperative phase of surgery; generating a 3D image of the spine from 2D images intraoperatively (e.g., Computer Tomography (CT) images); registering the 3D images at both the preoperative phase and the intraoperative phases of surgery; and adjusting the patient posture intraoperatively or the spinal alignment in the fused segment intraoperatively to improve the postural surgical outcomes.

Embodiments of the present disclosure provide technical solutions to one or more of the problems of (1) inaccuracy associated with comparing 2D images, (2) multiple adjustments to patient posture during a surgery or surgical procedure, (3) inconsistency between preoperative and intraoperative spinal positions, and (4) inconsistency between the executed surgery and the surgical plans due to lack of visualizations or guidelines intraoperatively.

Turning first to FIG. 1, a block diagram of a system 100 according to at least one embodiment of the present disclosure is shown. The system 100 may be used to capture and/or generate 2D or 3D images of anatomical elements in a first posture of a patient, capture and/or generate 2D or 3D images of the patient in a second posture, compare the 2D or 3D images, provide recommendations to adjust the posture of the patient based on the comparison, and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200, 300, 400, and/or 500 described herein, or of any other methods. The memory 106 may store, for example, instructions and/or machine learning models that support one or more functions. For instance, the memory 106 may store content (e.g., instructions and/or machine learning models) that, when executed by the processor 104, enable image processing 120, comparison 122, transformation 124, and/or registration 128. Such content may, in some embodiments, be organized into one or more applications, modules, packages, layers, or engines. Alternatively or additionally, the memory 106 may store other types of data (e.g., machine learning models, artificial neural networks, etc.) that can be processed by the processor 104 to carry out the various methods and features described herein. Thus, although various components of memory 106 are described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102. In some embodiments, the user interface 110 may be or comprise a virtual reality or augmented reality system that allows superimposing different postures and alignment virtually.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 200, 300, 400, and/or 500 described herein. The system 100 or similar systems may also be used for other purposes.

Figure 2:
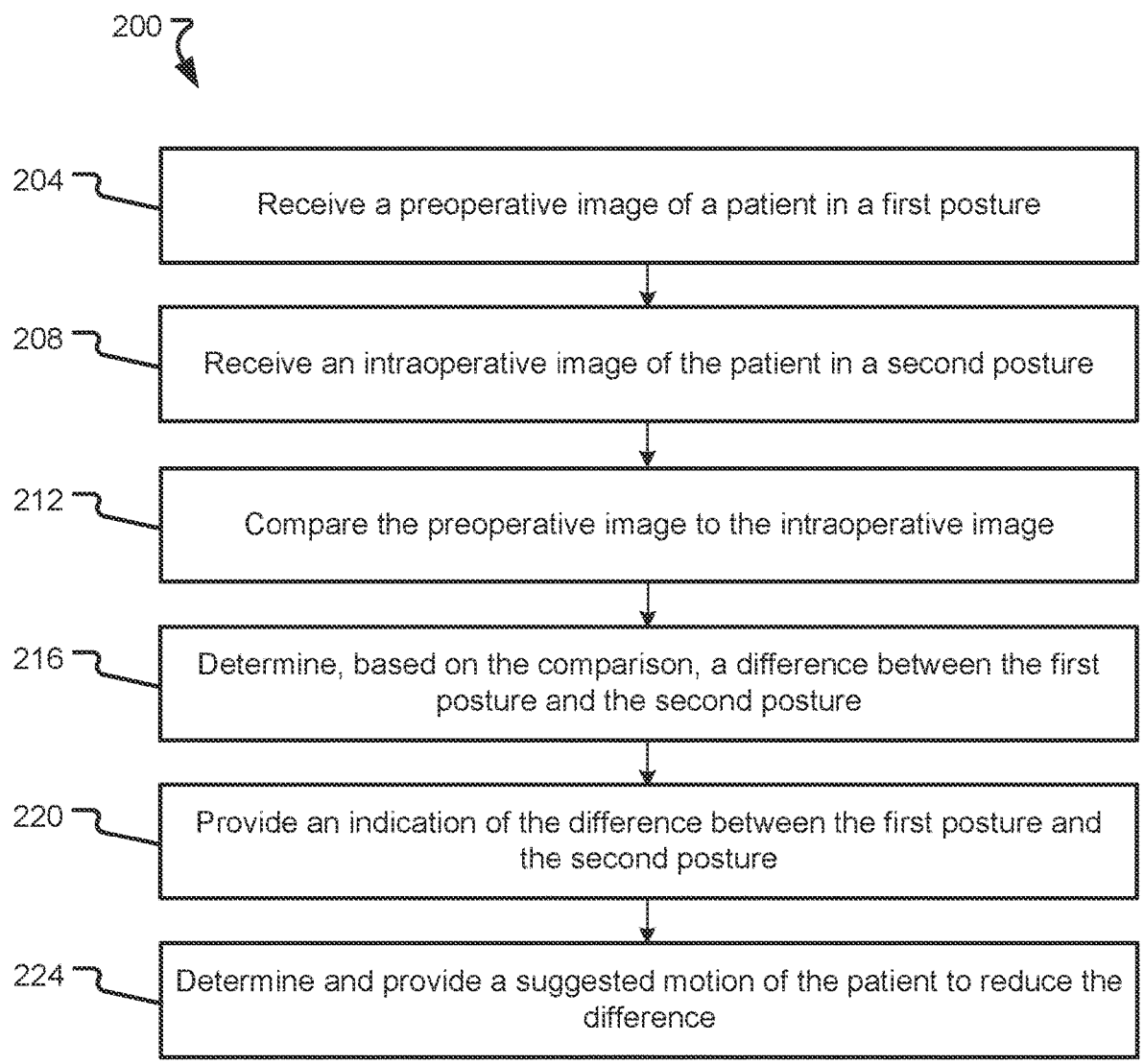
FIG. 2 is a flowchart according to at least one embodiment of the present disclosure.

FIG. 2 depicts a method 200 that may be used, for example, to determine a difference between a first posture and a second posture of anatomical elements of a patient and suggest a change in position of the patient to reduce the difference.

The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 200. The at least one processor may perform the method 200 by executing elements stored in a memory such as the memory 106. The elements stored in the memory and executed by the processor may cause the processor to execute one or more steps of the method 200 described below. One or more portions of the method 200 may be performed by the processor executing any of the contents of memory, such as an image processing 120, a comparison 122, a transformation 124, and/or a registration 128.

The method 200 comprises receiving a preoperative image of a patient in a first posture (step 204). The preoperative image may be an image or image information captured by a system (e.g., the system 100) and/or one or more components thereof (e.g., imaging devices 112). In some embodiments, the preoperative image may be saved in a database (e.g., a database 130), with the step 204 receiving the preoperative image from the database. The preoperative image may be accessed or received (e.g., by a processor 104) intraoperatively (i.e., during a surgery or surgical procedure) or preoperatively (e.g., during a planning phase of the surgery). The preoperative image may be a 2D image of the patient, such as an X-ray image (i.e., a calibrated radiograph) and may depict one or more anatomical elements (e.g., vertebrae, ribs, spine and/or components thereof, combinations thereof, etc.) of with the patient. In some embodiments, the preoperative image may comprise a plurality of 2D images (e.g., an imaging source and imaging detector may respectively generate and capture X-rays at various angles or directions with the patient therebetween when the patient is in the first posture to generate a plurality of calibrated radiographs) with each 2D image depicting a different view of the patient (and/or the one or more anatomical elements).

The first posture of the patient may be a standing position (e.g., the patient is standing up straight on both legs). In some embodiments, the standing position may be a different posture for the patient than the posture of the patient intraoperatively, such that the patient and/or the one or more anatomical elements of the patient depicted in the 2D image(s) are positioned differently when the patient is in the first posture than when the patient is not in the first posture (such as when the patient is in a supine position or any other position during the surgery or surgical procedure).

The method 200 also comprises receiving an intraoperative image of the patient in a second posture (step 208). The intraoperative image of the patient may be captured using one or more components of the system (e.g., an imaging device 112) while the patient is in a second posture. The intraoperative image may be or comprise a 2D image of the patient, such as an X-ray image. In some embodiments, the intraoperative image may comprise additional or alternative views of the patient (and/or the anatomy of the patient) than the preoperative image. In some embodiments, the intraoperative image may be or comprise a plurality of intraoperative images taken at different times during a procedure (e.g., a first intraoperative image may be received at a first time, a second intraoperative image may be received at a second time, etc.).

The second posture may be different than the first posture. For example and as mentioned in the step 204, while the patient may be standing in the first posture, the patient may be in a different position in the second posture, such as the supine position, a prone position, a lateral position, or some other non-standing position. As such, the intraoperative image may depict the patient and/or the one or more anatomical elements of the patient in the second posture differently (e.g., at different angles, in different poses relative to other anatomical elements, etc.) than in the first posture.

The method 200 also comprises comparing the preoperative image to the intraoperative image (step 212). In some embodiments, the step 212 may implement one or more comparisons 122 to compare the preoperative image to the intraoperative image. In some embodiments, the step 212 may use one or more transformations 124) to transform the preoperative image and/or the intraoperative image before comparison. For instance, the preoperative image and/or the intraoperative image may be converted from 2D X-ray images into 3D models of the patient and/or one or more anatomical elements before the comparison. The resulting 3D models (the derivations of which are further discussed below with reference to FIGS. 3 and 4 and respective methods 300 and 400) may be passed into the comparison 122, which may compare the two 3D models. For example, the comparison may be or comprise machine learning models that identify one or more limbs or other features of the patient and/or each of the one or more anatomical elements within one of the 3D models (using, for example, artificial intelligence or machine learning models trained on historical data, medical imaging data/information, and/or other image information) and match each portion of the patient and/or anatomical element to a respective portion of the patient and/or anatomical element in the other 3D model. Each of the 3D models may be or comprise information relating to the relative pose of patient (and/or patient anatomy) in the first posture and the second posture, respectively. In some embodiments, the step 212 may use one or more registrations 128 to map one 3D model (e.g., the 3D model associated with the patient in the first posture) to the other 3D model (e.g., the 3D model associated with the patient in the second posture) or vice versa, such that coordinates associated with both 3D models are represented in the same coordinate system.

The method 200 also comprises determining, based on the comparison, a difference between the first posture and the second posture (step 216). Following from the step 212, the step 216 may take the 3D models and determine a difference in the poses of one or more portions of the patient and/or the one or more anatomical elements in the preoperative image with the one or more portions of the patient and/or the one or more anatomical elements in the intraoperative image. The difference between the 3D model representing first posture and the 3D model representing the second posture may be determined by calculating a percent difference and/or a pose difference between the one or more portions of the patient and/or the one more anatomical elements depicted by the 3D models. More specifically, the step 216 may use a comparison 122 that determines differences between the coordinates of the one or more portions of the patient and/or the one or more anatomical elements of the 3D model associated with the first posture and the coordinates of the one or more portions of the patient and/or the one or more anatomical element of the 3D model associated with the second posture. In some embodiments, the preoperative image and the intraoperative image may be mapped into a common coordinate system, and the comparison may include calculating a difference in coordinates between an anatomical element in the preoperative image with the same anatomical element in the intraoperative image, to determine a difference therebetween.

In some embodiments, the comparison may compare coordinates differences to a threshold value and may tag or identify each of the one or more anatomical elements whose coordinate differences are above a threshold value (e.g., greater than a 0.5% difference, greater than a 1% difference, greater than a 2% difference, greater than a 5% difference etc.). Additionally or alternatively, the system may identify the coordinate differences that fall below a threshold value. The threshold value may be a value predefined by the system, and/or a value retrieved from the database. The threshold value may represent a level of safety defined by and/or associated with the system. For instance, the threshold value may be 2%, which may indicate that the system defines a greater than 2% difference between the coordinates of one or more anatomical elements in the preoperative image and coordinates of the one or more anatomical elements in the intraoperative image (when both coordinates are mapped to a common coordinate system) as a safety risk to the patient. At a greater than 2% difference, the patient may be positioned, for example, intraoperatively (i.e., in the second posture) such that patient and/or one or more anatomical elements (e.g., the spine) are aligned differently enough than how they are aligned when the patient is in the first posture (e.g., standing) that subsequent surgery or surgical procedures on the patient and/or one or more anatomical elements of the patient may have an adverse or unwanted effect on the patient (e.g., at greater than 2% difference, drilling a hole in a vertebra of the spine when the patient is in the second posture would result in post-operative patient discomfort). Other problems that may be associated with such mismatch between the postures include fusing the spine in an alignment that is not natural to the patient posture or fusing the spine in an alignment or manipulating the vertebral body in a manner that is not in agreement with the unfused adjacent or non-adjacent segments of the spine and pelvis, which may lead to patient dissatisfaction post-operatively.

The method 200 also comprises providing an indication of the difference between the first posture and the second posture (step 220). The indication of the difference may be presented to a user (e.g., a surgeon) via displaying the 3D models on a user interface (e.g., a user interface 110), such that the user may see the difference between the 3D models (and, by extension, the difference between the pose of the one or more anatomical elements of the patient in the first posture and the pose of the one or more anatomical elements of the patient in in the second posture). In some embodiments, the system may display areas of overlap on the 2D or 3D models in a first color (e.g., blue), while also marking locations where the 2D or 3D models do not overlap in a second color (e.g., red). In some embodiments, the rendering to the user interface may include highlights, marks, or other visual indicia on coordinates (and/or the one or more anatomical elements corresponding to the coordinates) that are above (or fall below) the threshold value. For instance, coordinates of the one or more portions of the patient and/or the one or more anatomical elements that do not meet the threshold requirements may be shown in a different color in the rendering to the user interface.

The method 200 also comprises determining and providing a suggested motion of the patient to reduce the difference (step 224). The step 224 may implement one or more transformations (e.g., transformations 124) that receive the difference in the first posture of the patient and the second posture of the patient and determine a movement of one or more portions of the patient, a movement of at least one of the one or more of the anatomical elements, a movement of the table or surface by which the patient is supported (e.g., an operating room table), and/or any other movement or adjustment that can be made to directly or indirectly change the posture of the patient (and/or the poses of one or more anatomical elements). In some embodiments, the transformations may optimize the movement by minimizing the distance between the coordinates of the preoperative image with the coordinates of the intraoperative image. In some embodiments, the coordinate differences may be minimized by the transformations determining a movement that would adjust the coordinates of the one or more portions of the patient and/or the one or more anatomical elements of the intraoperative image (or 3D model) to more closely match the respective coordinates of the one or more portions of the patient and/or one or more anatomical elements of the preoperative image (or 3D model). For instance, the transformation may determine a patient movement necessary to transform the coordinates of the one or more anatomical elements of the intraoperative image into the same coordinates as the coordinates of the one or more anatomical elements for the preoperative image and may generate a corresponding recommended motion of the patient to achieve the transformation. The resulting recommended motion may be provided via, for example, the user interface.

For instance, the recommended motion may be displayed on the user interface to permit a user (e.g., a surgeon, a member of surgical staff, etc.) to carry out the recommended motion (e.g., the transformation determines that moving the patient's body 3 inches in a first direction will minimize the determined coordinate difference and displays "move patient's body 3 inches in the first direction" on the user interface).

In some embodiments, one or more steps of the method 200 may be repeated after the suggested motion has been provided (and/or the patient has been moved). For instance, after the patient is moved or adjusted, the steps 208-224 may be subsequently performed on the patient in the new pose. In other words, the patient may be moved or adjusted, and the system may implement the method 200 again including capturing the new posture of the patient (and/or the new pose(s) of the one or more anatomical elements of the patient). The new posture can be compared with the preoperative pose (i.e., the first posture), a difference determined, and an additional suggested motion provided by the system. In some embodiments, the system may implement the method 200 repeatedly (or the user and/or processor may cause the method 200 to be carried out repeatedly) until the intraoperative posture of the patient matches or is sufficiently close to the preoperative posture of the patient.

The present disclosure encompasses embodiments of the method 200 that comprise more or fewer steps than those described above, and/or one or more steps that are different than the steps described above.

Figure 3:
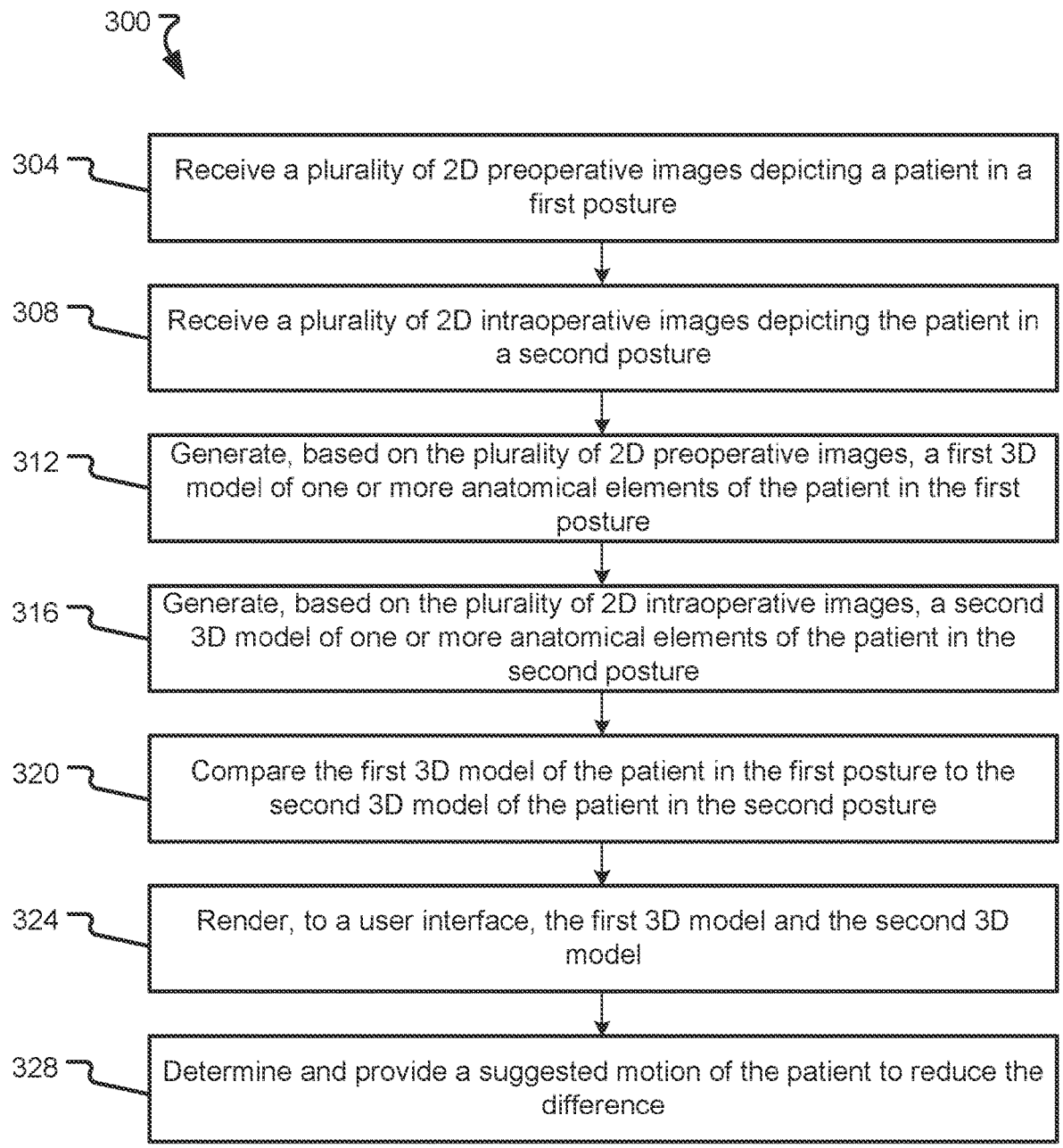
FIG. 3 is a flowchart according to at least one embodiment of the present disclosure.

FIG. 3 depicts a method 300 that may be used, for example, construct and compare two 3D images of a patient to determine a difference in pose of one or more anatomical elements and provide a suggested motion to reduce the difference.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing elements stored in a memory such as the memory 106. The elements stored in the memory and executed by the processor may cause the processor to execute one or more steps of the method 300 described below. One or more portions of a method 300 may be performed by the processor executing any contents of the memory, such as an image processing 120, a comparison 122, a transformation 124, and/or a registration 128.

The method 300 comprises receiving a plurality of 2D preoperative images depicting a patient in a first posture (step 304). The plurality of 2D preoperative images, which may be, for example, X-rays, fluoroscopy images, or the like, may be captured using an imaging source and corresponding imaging detector or any other imaging device (e.g., imaging devices 112), and may depict one or more anatomical elements of the patient while the patient is in the first posture. In some embodiments, the plurality of 2D preoperative images may depict various views or angles of the one or more anatomical elements (e.g., the imaging source and imaging detector may sweep around the body of the patient capturing the plurality of 2D preoperative images of the one or more anatomical elements). The one or more anatomical elements may comprise bone (e.g., vertebrae, ribs, etc.), soft tissues, combinations thereof, and/or the like.

In one embodiment, the one or more anatomical elements comprise one or more portions or sections of the human spine (e.g., the cervical spine section, the thoracic spine section, the lumbar spine section, the sacral spine section, combinations thereof, etc.)

The first posture may depict the patient in a standing position. In some embodiments, the first posture may be a posture different from the posture the patient will be positioned intraoperatively (i.e., during a surgery or surgical procedure). As such, the pose of the one or more anatomical elements may also be different between the first posture and the intraoperative posture of the patient. In some embodiments, the differences between the two postures may be used to quantitatively determine how much change is imparted due to the change in the posture and what is the remaining required postural changes are to attain an optimal adjustment to the spine. Further, the difference may be used to determine the relative alignment of the sections of the anatomical elements of the patient subject to the surgery or surgical procedure with the sections of the anatomical elements of the patient that are not subject to the surgery or surgical procedure.

The method 300 also comprises receiving a plurality of 2D intraoperative images depicting the patient in a second posture (step 308). The 2D intraoperative images may be captured during the surgery or surgical procedure (or during the planning phase before the surgery or surgical procedure after the patient has been placed into the second posture) and may depict the one or more anatomical elements. In some embodiments, the second posture may be a non-standing position (e.g., a supine position, a prone position, etc.) or any other position different from the first posture, such that the anatomy of the patient (including the one or more anatomical elements) may be shifted from the first posture (e.g., a standing position). The plurality of 2D intraoperative images may be or comprise X-rays, fluoroscopy images, 2D CT images, and/or other 2D images or image information.

The method 300 also comprises generating, based on the plurality of 2D preoperative images, a first 3D model of one or more anatomical elements of the patient in the first posture (step 312). The step 312 may make use of image processing (e.g., image processing 120) that receives the plurality of 2D preoperative images and output a 3D model of one or more anatomical elements depicted in the plurality of 2D preoperative images. In some embodiments, the image processing may receive the plurality of 2D preoperative images (which may depict, for example, one or more sections of the human spine) as well as additional information related to the one or more anatomical elements (e.g., an atlas-based shape model, a conditional random field, etc.) to output the first 3D model. In some embodiments, the image processing may be or comprise an artificial intelligence or machine learning model (e.g., a Convolutional Neural Network (CNN)) that has been trained on historical data and/or other image data to process the plurality of 2D images and generate the first 3D model therefrom. The other imaging data may, in some instances, comprise a plurality of images from a plurality of different patients who may have undergone similar or the same surgeries or surgical procedures. For instance, the one or more anatomical elements may comprise to the human spine with the surgery being directed toward a spinal procedure. The image processing used to render the 3D model may be trained on images of the spine from a plurality of other patients who each underwent a similar or the same spinal procedure. Similarly, a surgical procedure on a rib may use a different algorithm, machine learning model, and/or CNN trained on images of the rib from a plurality of different patients. In some embodiments, the CNN may be trained on a images or other information related to a plurality of patient similar to or who share similar traits with the patient (e.g., a patient who is 183 centimeters (cm) tall may have an on-average more elongated spine with different vertebrae spacing than someone less than 183 cm tall, and the CNN used in the step 312 may be trained on images of spines of patients who are 183 cm or taller), such that the results of the CNN are more accurate than if images of anatomical elements of a wider population variance were used.

The method 300 also comprises generating, based on the plurality of 2D intraoperative images, a second 3D model of one or more anatomical elements of the patient in the second posture (step 316). In some embodiments, the step 316 may be similar to the step 312. For instance, the step 316 may use image processing that receives the plurality of 2D intraoperative images (as well as additional information related to the one or more anatomical elements) as inputs and output a 3D model of the one or more anatomical elements. Since the 3D model is generated based on the plurality of 2D intraoperative images, the 3D depicts the pose of the one or more anatomical elements when the patient is in the second posture (i.e., how the patient is oriented during the surgery or surgical procedure or during a planning phase) that is different form the first posture. In some embodiments, the 3D models of the one or more anatomical elements generated from both the plurality of 2D preoperative images and the plurality of 2D intraoperatively images may respectively have a separate coordinate system associated therewith.

The method 300 also comprises comparing the first 3D model of the patient in the first posture to the second 3D model of the patient in the second posture (step 320). In some embodiments, the step 320 may make use of one or more comparisons (e.g., comparisons 122) to compare the first 3D model with the second 3D model. The comparisons may receive both the first 3D model and the second 3D model as inputs and output a comparison. In some embodiments, the comparisons may map coordinates associated with the first 3D model into the coordinate system of the second 3D model, or vice versa. In some embodiments, the comparisons may map both coordinates associated with the first 3D model and coordinates associated with the second 3D model into a third coordinate system (e.g., a coordinate system associated with the surgical environment).

The comparison produced by the comparisons may be or comprise information related to the amount of similarity and/or the amount of difference between the first 3D model and the second 3D model. In some embodiments, the comparisons may overlay the first 3D model and the second 3D model, and determine information related to the similarities and differences therebetween based on the overlaying. For instance, the comparisons may identify and/or tag areas where the first 3D model overlaps with the second 3D model (and vice versa). Additionally or alternatively, the comparisons may identify and/or tag areas where the first 3D model does not overlap with the second 3D model. In some embodiments, the comparisons may implement one or more artificial intelligence and/or machine learning models to identify each of the one or more anatomical elements in the first 3D model and match each of the one or more anatomical elements to the corresponding one or more anatomical elements in the second 3D model (or vice versa). The artificial intelligence and/or machine learning models may be trained on historical data (e.g., data stored in the database) related to the surgery or surgical procedure, medical image data (e.g., other medical images depicting the one or more anatomical elements from a plurality of different patients) and/or on other image information (e.g., information about the general shapes of anatomical elements, information about the pixel density associated with the anatomical elements when depicted images or 3D models are rendered to an interface, etc.) to identify each of the one or more anatomical elements in both the first 3D model and the second 3D model and determine areas of overlap and areas of non-overlap.

In some embodiments, the comparisons (e.g., using a CNN) may output a confidence score along with the comparison information. The confidence score may be or comprise a quantitative indicator (e.g., a value or range of values, a percent, etc.) indicating the level of uncertainty associated with the comparison. In some embodiments, the confidence score may be compared with a threshold value, with the threshold value being a predefined value below which the system deems the comparison result untrustworthy (i.e., not accurate enough to rely on in determining the similarities and differences between the first 3D model and the second 3D model). Alternatively, the confidence score may be or comprise an error estimate that may rise above a threshold value, which may indicate that the error value associated with the comparison is too high to be considered trustworthy. In some embodiments, when the confidence score falls below the threshold value (or in some embodiments, when the error estimate rises a above the threshold value), the method 200 may implement the step 320 again, but use a different comparison content trained on different data to calculate a comparison with an acceptable confidence score or error estimate (i.e., a comparison that produces a confidence score above a threshold value or an error estimate below a threshold value). In some embodiments, the step 320 may comprise running the comparison on multiple comparisons trained on different data sets and use the results from the comparisons that generated the highest confidence score (or in some embodiments lowest error estimate).

The method 300 also comprises rendering, to a user interface, the first 3D model and the second 3D model (step 324). The step 324 may render the first 3D model and the second 3D model to a user interface (e.g., a user interface 110), such that the first 3D model and the second 3D model may be viewed by a user (e.g., a surgeon, a surgical staff member, etc.). In some embodiments, the renderings may include visual indicia of the areas of overlap and/or areas of non-overlap as identified by the comparisons in the step 320. The visual indicia of the areas of overlap and/or the areas of non-overlap may facilitate the user in understanding the difference between the pose of the one or more anatomical elements when the patient is in the first posture (e.g., a standing position prior to surgery) and the pose of the one or more anatomical elements when the patient is in the second posture (e.g., a non-standing position during surgery). In some embodiments, the visual indicia may comprise different colors or intensities in the renderings to distinguish areas of overlap from areas of non-overlap (and vice versa). For example, the areas of overlap may be rendered in a first color (e.g., yellow), while the areas of non-overlap may be rendered in a second color (e.g., purple).

The method 300 also comprises determining and providing a suggested motion of the patient to reduce the difference (step 328). The step 328 may use or implement one or more transformations (e.g., transformations 124) to determine a suggested movement of the patient to reduce the areas of non-overlap between the first 3D model and the second 3D model. For instance, the transformations may determine a movement of the patient (and/or one or more anatomical elements) from a first position to a second position that would minimize the difference between the first 3D model and the second 3D model with respect to a first vertebra and provide the suggestion to the user (e.g., turn the patient from a first side to a second side, roll or rotate the patient, move patient in one or more directions on a surgical table, move the knees of the patient from a first pose to a second pose, etc.). For example, in one embodiment the step 328 may determine that the difference may be reduced when the patient lies on his right-hand side (when the patient may be lying on his left-hand side) and may suggest that the patient be moved or rotated onto his right-hand side.

In some embodiments, the results of the transformations may be provided to the user (e.g., via a user interface). In some embodiments, the results of the transformations may be additionally or alternatively sent to one or more other components of the system (e.g., to a navigation system 118). The one or more other components of the system may automatically adjust or cause other components to automatically adjust based on the recommendation of the transformations (e.g., the transformation recommends moving the patient from the first height on the table to a second height, and the recommendation is sent to a navigation system that causes a table on which the patient is resting to move such that the patient moves from the first height to the second height).

The present disclosure encompasses embodiments of the method 300 that comprise more or fewer steps than those described above, and/or one or more steps that are different than the steps described above.

Figure 4:
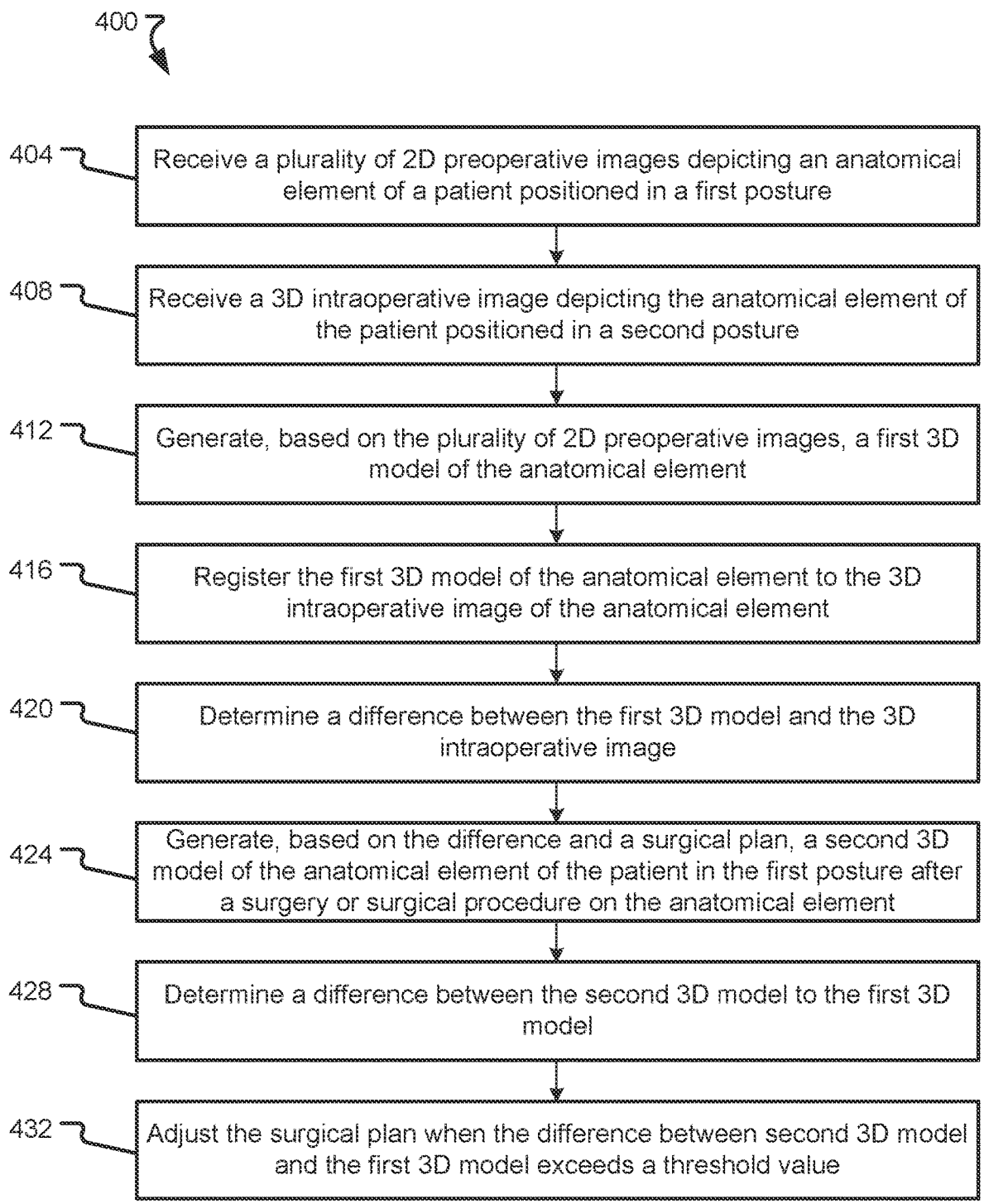
FIG. 4 is a flowchart according to at least one embodiment of the present disclosure.

FIG. 4 depicts a method 400 that may be used, for example, to compare 3D models of a patient in different positions and adjust a surgical plan based on the comparison.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing elements stored in a memory such as the memory 106. The elements stored in the memory and executed by the processor may cause the processor to execute one or more steps of a function as shown in the method 400 described below. One or more portions of the method 400 may be performed by the processor executing any of the contents of memory, such as an image processing 120, a comparison 122, a transformation 124, and/or a registration 128.

The method 400 comprises receiving a plurality of 2D preoperative images depicting an anatomical element of a patient positioned in a first posture (step 404). The plurality of images may depict the anatomical element at a variety of angles or views. For example, the anatomical element may be a vertebra, and the plurality of 2D preoperative images may depict one or more views of the top, bottom, left, right, front, and/or back of the vertebra. The plurality of images may be captured when the patient is positioned in the first posture, which may be a standing posture or other posture different from the posture the patient may be in during a surgery or surgical procedure.

The method 400 also comprises receiving a 3D intraoperative image depicting the anatomical element of the patient positioned in the second posture (step 408). The 3D intraoperative image may be or comprise image information related to the shape, volume, and/or contours of the anatomical object (e.g., a CT scan of the anatomical element). The second posture of the patient may be a non-standing position (e.g., a prone position, a supine position, etc.), and may correspond to the intraoperative position the patient (i.e., the position of the patient during the surgery or surgical procedure).

The method 400 also comprises generating, based on the plurality of 2D preoperative images, a first 3D model of the anatomical element (step 412). In some embodiments, the step 412 may be similar to or the same as the step 312. For instance, the step 412 may utilize or implement image processing (e.g., image processing 120) to take the plurality of 2D preoperative images as inputs and output the first 3D model. In some embodiments, the image processing may be or comprise machine learning models trained on data associated with the anatomical element (e.g., trained on other preoperative images of the anatomical element taken from a plurality of other patients, trained on 3D models of the anatomical element, etc.) that can identify the types of anatomical elements depicted in the plurality of 2D preoperative images and interpolate the 2D images into the first 3D model. As an example, the machine learning model may receive 2D images of a vertebra, identify that the 2D images depict a vertebra, and apply a first interpolation to the vertebra. In another example, the machine learning model may receive 2D images a rib, identify that the 2D images depict a rib, and apply a second interpolation to the rib, with the second interpolation different from the first interpolation. The different interpolations may be based on the training of the model (e.g., the model may learn based on the training data that the first interpolation for vertebra is inappropriate or not optimal for transforming a plurality of 2D images depicting a rib).

The method 400 also comprises registering the first 3D model of the anatomical element to the 3D intraoperative image of the anatomical element (step 416). The step 416 may use one or more registrations (e.g., registrations 128) to complete the registration of the first 3D model of the anatomical element to the 3D intraoperative image of the anatomical element (or vice versa). In some embodiments, the registration may comprise artificial intelligence or machine learning models that receive the first 3D model and the 3D intraoperative image an identify and match one or more portions of the anatomical element as depicted in the first 3D model to corresponding one or more portions of the anatomical element depicted in the 3D intraoperative image. For example, the anatomical element may be a vertebra, and the image processing may detect that the anatomical element is a vertebra and identify one or more portions of the vertebra (e.g., a vertebral body, a facet, a transverse process, a facet joint, an articular process, a spinous process, etc.) in both the first 3D model and the 3D intraoperative image, and map coordinates associated with the one or more sections in the first 3D model to the corresponding coordinates of the one or more section in the 3D intraoperative image (or vice versa).

The method 400 also comprises determining a difference between the first 3D model and the 3D intraoperative image (step 420). The difference between the first 3D model and the 3D intraoperative image may be determined based on the difference between the coordinates of the anatomical element (or one or more portions thereof) of the first 3D model with the coordinates of the anatomical element (or one or more portions thereof) of the 3D intraoperative image in a common coordinate system (e.g., a coordinate system where the first 3D model is registered to the 3D intraoperative image, or vice versa, a common coordinate system into which both the first 3D model and the 3D intraoperative image are mapped, etc.). The step 420 may use one or more comparisons (e.g., comparisons 122) to receive the first 3D model and the 3D intraoperative image and output information related to the difference in coordinates between the first 3D model and the 3D intraoperative image. In some embodiments, the comparisons may output a determined difference between the coordinates (e.g., a percent difference between the coordinates, an average distance between each of the coordinates, etc.). In some embodiments, the comparisons may output the largest coordinate difference of all the coordinate comparisons, the smallest coordinate difference of all the coordinate comparisons, an average distance between the coordinates of the first 3D model and the coordinates of the 3D operative image, combinations thereof, and/or the like.

In some embodiments, the coordinate difference may be based on one or more portions of the anatomical element identified by the comparisons. For example, the anatomical element may be a vertebra, and the comparisons may receive, among other things, coordinates of the vertebral body of the vertebra of both the first 3D model and the 3D intraoperative image, and coordinates of the facet joint as of both the first 3D model and the 3D intraoperative image. The comparisons may compare the sets of coordinates each associated with the vertebral body and determine that the coordinates have a first average distance of separation, and may also compare the sets of coordinates each associated with the facet joint and determine that the coordinates have a second average distance of separation. In some embodiments, the comparisons may output the first and second average distances.

Both the first and second average distances of separation may provide information useful for determining a difference in pose of the vertebra between the first 3D model (which corresponds to the pose of the vertebra when the patient is in the first posture such as a standing position) and the 3D intraoperative image (which corresponds to the pose of the vertebra when the patient is in the second posture such as a non-standing position). In some embodiments, the system may compare the average distance determinations against threshold distance values, and may generate alerts (e.g., visual indicia of a warning rendered on a user interface, auditory indicia in the form of a siren or alarm, etc.) when the average distance determinations exceed threshold distance values. The exceeding of the threshold distance values may indicate that the pose of the vertebra (and/or sections or portions thereof) during the procedure (or as positioned during a planning phase of the surgery or surgical procedure) is not sufficiently close to the pose of the vertebra before the procedure, which may allow for adjustment of the pose of the vertebra during the planning phase or during the implementation of a surgical plan (i.e., intraoperatively). The comparison and determination of pose difference between the first 3D model and the 3D intraoperative image beneficially enables for adjustment to the surgical plan (as discussed below) to reduce inaccuracies during surgery.

The method 400 also comprises generating, based on the difference and a surgical plan, a second 3D model of the anatomical element of the patient in the first posture after a surgery or surgical procedure on the anatomical element (step 424). The step 424 may use one or more transformations (e.g., transformations 124) to apply the surgical plan to 3D intraoperative image to produce a simulated model of the anatomical element after the surgery or surgical procedure has been conducted. In some embodiments, such as those where the surgery or surgical procedure results in multiple changes in pose, the transformations may apply each change consecutively to the 3D intraoperative image to result in a simulated model depicting the anatomical element after the surgery or surgical procedure. For instance, during a spinal surgery where a vertebra is drilled into, a screw is inserted into the drilled hole, and a rod is threaded through the screw, the transformations may predict how each step of the surgical process impacts the 3D intraoperative image and produces a simulated model of the vertebra after a hole is drilled therein, a screw is inserted therein, and a rod is passed through the screw. In some embodiments, the transformations may be or comprise an artificial neural networks, artificial intelligence models, or a machine learning models trained on data related to similar surgical procedures, as well as resulting poses of anatomical elements upon which the surgical procedures are conducted. Returning to the example vertebra, the transformations may be trained on medical images of vertebrae of other patients to which the same or similar drilling, screw inserting, and/or rod threading had been applied, which may improve the accuracy of the simulated model of the anatomical element.

The step 424 may use the simulated model to along with the difference calculation to generate the second 3D model. In some embodiments, the step 424 may use a registration that receives the simulated model and the difference calculation as inputs and outputs the second 3D model. The registration may map the simulated model into the same coordinate system as the first 3D model (i.e., the coordinate system used to describe the patient in the first posture), factoring in any changes using the difference calculation to generate the second 3D model. As such, the second 3D model may depict a predicted outcome of the pose of the anatomical element when the patient is in the first posture after the surgery or surgical procedure has been performed on the anatomical element.

The method 400 also comprises determining a difference between the second 3D model and the first 3D model (step 428). In some embodiments, the step 428 may use one or more comparisons to compare the second 3D model (which may correspond to the predicted pose of the anatomical element after the surgery or surgical procedure when the patient is in the first posture) with the first 3D model (which may correspond to the modeled pose of the anatomical element when the patient is in the first posture based on images captured before surgery). The comparisons may compare coordinates of the second 3D model with coordinates of the first 3D model and determine distances therebetween. In some embodiments, the comparisons may return the distances between each of the coordinates. In other embodiments, the comparisons may return an average difference in distance across all compared coordinates. In some embodiments, the comparisons may be trained on data associated with the anatomical element, and may be configured to identify one or more sections of the anatomical element (e.g., a vertebral body, a facet joint, etc.) and determine the coordinate difference between one or more of the sections of the anatomical element in the first 3D model and the corresponding one or more sections of the anatomical element in the second 3D model.

The method 400 also comprises adjusting the surgical plan when the difference between the second 3D model and the first 3D model exceeds a threshold value (step 432). The step 432 may cause (e.g., by a computing device such as the computing device 102, by a processor such as the processor 104, etc.) the difference(s) returned by the comparisons in the step 428 to be compared to threshold value(s). The threshold value may be a predefined value and/or a value retrieved from the database. The threshold value may indicate a level of difference in the poses of the anatomical element above which the system determines that the surgical plan associated with the surgery or surgical procedure should be adjusted. The threshold value may a percentage (e.g., 0.2%, 0.5%, 1%, 2%, etc.) above which the difference between the second 3D model and the first 3D model is considered too great to carry out the current surgical plan. A difference is above the threshold value, for example, may indicate that the surgical plan is too greatly correlated with patient dissatisfaction (e.g., the surgical plan would result in the patient being uncomfortable in the first posture after the surgery).

In some embodiments, the comparison may compare multiple differences to multiple threshold values. The anatomical element, for example, may be a vertebra and the difference determination between the second 3D model and the first 3D model may return a first difference associated with a first section of the vertebra (e.g., a vertebral body) and a second difference associated with a second section of the vertebra (e.g., a facet joint). Each of the first and second differences may be compared to separate threshold values (which may be different predetermined values). In some embodiments, if one or more of the first and second difference exceeds the respective threshold values, the system may determine that the current surgical plan does not meet threshold requirements to be carried out.

When the difference exceeds the threshold value, the system may adjust or suggest an adjustment in the surgical plan. For instance, if the surgical plan comprises drilling into a vertebra at a first angle to a first depth, and the system determines that the difference exceeds the threshold value (which may indicate that such a surgical plan would result in a difference between the pose of the anatomical element before the surgery and the pose of the anatomical element after the surgery being too great, possibly leading to patient dissatisfaction or discomfort), the system may recommend or provide a change (e.g., the angle of the drilling from a first angle to a second angle, changing the drilling depth from the first depth to a second depth, etc.) such that the difference is minimized or otherwise falls below the threshold value. In some embodiments, the method 400 may conduct the steps 424 through 432 based on the recommended change to verify that the change lowers the difference below the threshold level. In some embodiments, the threshold values may vary depending on, for example, the type of surgery, the type of anatomical element, the patient (e.g., age, weight, height, etc. of the patent), combinations thereof, and/or the like. Additionally or alternatively, the system may provide an alert or other communication signal (e.g., a warning displayed on a user interface) to warn one or more users in the surgical environment that the threshold value(s) have been exceeded.

The present disclosure encompasses embodiments of the method 400 that comprise more or fewer steps than those described above, and/or one or more steps that are different than the steps described above. Further, while the method 400 is discussed with reference to a single anatomical element, it is to be understood that additional anatomical elements may present in the received images and may be subsequently processed according to the method 400. For instance, the images received in the method 400 may depict a portion or the entirety of the human spine (which may comprise a plurality of anatomical elements such as vertebrae), and the portion or entirety of the human spine may be processed in accordance with one or more steps of the method 400.

Figure 5:
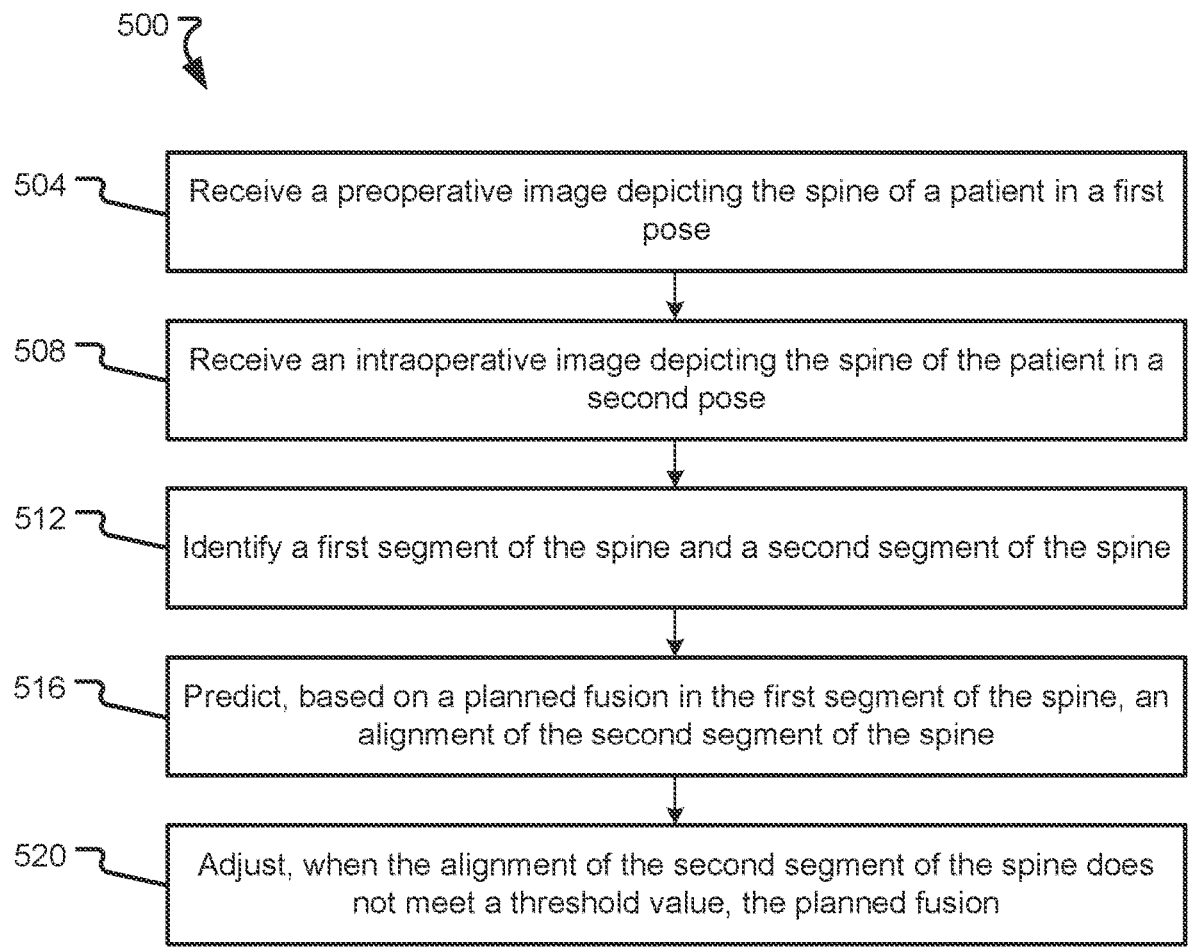
FIG. 5 is a flowchart according to at least one embodiment of the present disclosure.

FIG. 5 depicts a method 500 that may be used, for example, to determine a difference in alignment of an unfused segment of the spine of a patient based on the manipulation of a fused portion of the spine of the patient.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing elements stored in a memory such as the memory 106. The elements stored in memory and executed by the processor may cause the processor to execute one or more steps of a function as shown in method 500. One or more portions of the method 500 may be performed by the processor executing any of the contents of the memory, such as an image processing 120, a comparison 122, a transformation 124, and/or a registration 128.

The method 500 comprises receiving a preoperative image depicting the spine of a patient in a first pose (step 504). The preoperative image may be similar to or the same as any other preoperative image discussed herein. For example, the preoperative image may be or comprise a 2D or a 3D image. In some embodiments, the preoperative image may comprise one or more 2D or 3D depictions of the spine. The spine may comprise a plurality of unfused segments (e.g., vertebrae that have not been fused or otherwise connected to one another), as well as a plurality of planned fused segments (e.g., vertebrae that will be fused together). In some embodiments, the preoperative image may be transformed or otherwise changed into 2D or 3D models of the spine (or portions thereof). The first pose may be the pose associated with the patient while the patient is in a standing position.

The method 500 also comprises receiving an intraoperative image depicting the spine of the patient in a second pose (step 508). The intraoperative image may be similar to or the same as any other intraoperative image discussed herein. For example, the intraoperative image may be or comprise a 2D or a 3D image. In some embodiments, the intraoperative image may comprise one or more 2D or 3D depictions of the spine. In some embodiments, the intraoperative image may be transformed or otherwise changed into 2D or 3D models of the spine (or portions thereof). The second pose may be the pose of the patient during the surgery or surgical procedure.

The method 500 also comprises identifying a first segment of the spine and a second segment of the spine (step 512). The first segment of the spine may comprise one or more vertebrae on which a surgery or surgical procedure is to be performed (e.g., a spinal fusion). The second segment of the spine may be or comprise one or more vertebrae adjacent to the first segment of the spine (and/or to the vertebrae on which the surgical fusion is to be performed). In some embodiments, the second segment of the spine may not be adjacent to the first segment of the spine, and may be positioned further up or down the spinal column with respect to the first segment of the spine. In some embodiments, the first and second segments of the spine may be identified by passing the preoperative and/or intraoperative images through content stored in the memory 106 (e.g., machine learning models, convolutional neural networks, etc.). In some embodiments, the content (e.g., machine learning models, image processing, etc.) may also use the surgical plan to identify the first segment and/or the second segment of the spine. Additionally or alternatively, the content may identify other segments or anatomical elements of the spine (e.g., rods and pins from previous spinal procedures). In some embodiments, the first and second segments of the spine may be identified in both the preoperative image and the intraoperative image. In such embodiments, the first and second segments of the spine in the preoperative image and the intraoperative image may be rendered to a user interface (such as a computer screen or other display), such that users in the surgical environment (e.g., a surgeon, surgical staff, etc.) may view depictions of both the first and second segments of the spine in both a preoperative and intraoperative alignment. In other words, the rendering to the display may allow a surgeon to view the spine (as well as the first and second segments thereof) in both the preoperative pose and the intraoperative pose.

The method 500 also comprises predicting, based on a planned fusion in the first segment of the spine, an alignment of the second segment of the spine (step 516). The planned fusion may be a fusion (e.g., a joining) of two or more vertebrae in the first segment of the spine. In some embodiments, the first segment of the spine may comprise all vertebrae to be fused. The predicting may comprise simulating the introduction of the planned fusion into the first segment of the spine. For instance, the planned fusion may be applied to one or more vertebrae in the first segment of the spine using content stored in the memory 106, such as a transformation 124. The transformation may be implemented using a machine learning model or artificial intelligence model that uses the surgical plan to predict an alignment of the first segment of the spine after the fusion has been conducted. That is, the content may determine how the alignment of the spine (and/or components thereof such as the second segment of the spine) changes based on the fusion. In some embodiments, the transformation may introduce the planned fused portion of the spine (e.g., the first segment of the spine) to the depictions or data associated with the second segment of the spine in the preoperative and/or intraoperative images. In other words, the transformation 124 may evaluate how the fusion of the first segment of the spine may impact or change the alignment and/or pose of the second segment of the spine post-operatively by simulating the fusion and determining how the second segment would change with respect to the first segment. In some embodiments, the transformation 124 may be a model trained on historical data of preoperative and/or intraoperative images from similar procedures.

In some embodiments, the determined alignment of the spine and/or components or segments thereof may be rendered to a user display, permitting the user to view the predicted alignment and/or pose of the first segment and/or the second segment as a result of the fusion. For example, the surgeon may be able to view the predicted fusion and the predicted alignment of the second segment (e.g., the vertebrae not subject to the fusion procedure) relative to the first segment (e.g., the vertebrae that have been fused) after of the fusion has been performed. In some embodiments, the fusion of the vertebrae may occur at more than one location on the spine. In such embodiments, the step 516 may predict the alignment of the second segment of the spine relative to some or all segments of the spine subject to the planned fusions.

The method 500 also comprises adjusting, when the alignment of the second segment of the spine does not meet a threshold value, the planned fusion (step 520). Continuing from the step 516, the alignment of the second segment of the spine may not align with the first segment of the spine after the planned fusion has been performed on the spine as predicted by the content of the memory 106. The step 520 may implement content of the memory 106, such as a comparison 122 that may take the planned fusion and the resulting alignment and compare the alignment to a threshold value. The threshold value may be similar to or the same as any threshold value mentioned herein. In some embodiments, after comparing to the threshold value, and after determining that the alignment does not meet the threshold value (e.g., the alignment is not an acceptable outcome for the surgical procedure), the step 520 may cause the surgical plan to be adjusted. In some embodiments, the step 520 may use one or more transformations 124 that change the surgical plan to reduce the difference between the desired alignment of the spine and the predicted alignment of the spine. For example, the transformations 124 may be or comprise artificial neural networks that receive the desired alignment and the predicted alignment and determine a change to the surgical plan that will reduce the difference between the desired alignment (which may be predetermined or determined by the transformation) and the predicted alignment. The transformations 124 may change one or more aspects of the surgery or surgical plan (e.g., an angle at which the vertebrae are drilled, number of vertebrae fused, pose of the vertebrae before fusion, pose of screws and/or rods inserted during the spinal fusion, etc.), or provide recommended adjustments of the same to the user, to improve the alignment of the spine post-operatively. In some embodiments, the transformations 124 may be trained on historical data (e.g., short-term and/or long-term data to determine the short-term and/or long-term changes of the unfused segments of the spine) to better determine the shape of the spine after the surgery or surgical procedure. In some embodiments, the transformations 124 may take the predicted alignment and predict how the further application of one or more surgical plans or strategies would change the alignment. In some embodiments, the transformations 124 may iteratively repeat the application of the different surgical plans, change aspects of the surgical plan, and/or change the pose of the segments of the spine until the alignment falls meets the threshold value or falls within a range of the threshold (e.g., a range where patient satisfaction is acceptable).

It is to be noted that while the description of FIG. 5 and the corresponding method 500 discusses aspects of the present disclosure with respect to the spine and vertebrae, it is to be understood that the method 500 could be implemented with any other anatomical element (e.g., ribs, pelvic bones, etc.).

As noted above, the present disclosure encompasses methods with fewer than all of the steps identified in FIGS. 2, 3, 4, and 5 (and the corresponding description of the methods 200, 300, 400, and 500), as well as methods that include additional steps beyond those identified in FIGS. 2, 3, 4, and 5 (and the corresponding description of the methods 200, 300, 400, and 500). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method, comprising:

receiving a preoperative image depicting the spine of a patient in a first posture;

receiving an intraoperative image depicting the spine of the patient in a second posture while the patient rests on a surgical table in an operating room;

comparing the preoperative image of the patient in the first posture with the intraoperative image of the patient in the second posture;

determining, based on comparing the preoperative image of the patient in the first posture with the intraoperative image of the patient in the second posture, a difference between the first posture and the second posture;

determining, based on the difference between the first posture and the second posture, an alignment of a first segment of the spine of the patient with a second segment of the spine of the patient;

providing, via a display in the operating room, a suggested intraoperative motion during a surgery or surgical procedure to move the patient on the surgical table from the second posture to a third posture to reduce the difference between the second posture and the first posture, wherein the suggested intraoperative motion is provided before a spine of the patient is surgically manipulated; and updating, when the alignment of the first segment with the second segment falls below a threshold value after the patient is moved to the third posture, a planned spinal fusion of the first segment.

2. The method of claim 1, further comprising:

providing an indication of the difference;

receiving an additional intraoperative image of the patient, wherein the additional intraoperative image of the patient is received after the patient is moved from the second posture to the third posture;

comparing the preoperative image of the patient in the first posture with the additional intraoperative image of the patient in the third posture; and determining, based on comparing the preoperative image of the patient in the first posture with the additional intraoperative image of the patient in the third posture, a difference between the first posture and the third posture.

3. The method of claim 1, wherein the preoperative image of the patient in the first posture comprises a two-dimensional (2D) image, and wherein the method further comprises:

generating, with the 2D image, a three-dimensional (3D) model of an anatomical element of the first segment of the spine of the patient; and comparing the 3D model of the anatomical element of the patient with a view of the anatomical element in the intraoperative image.

4. The method of claim 1, wherein the first segment of the spine is surgically manipulated, and wherein the second segment of the spine is not surgically manipulated.

5. The method of claim 1, wherein the preoperative image and the intraoperative image are provided as an input to an artificial neural network, and wherein the artificial neural network provides an output that is used to determine the difference between the first posture and the second posture.

6. The method of claim 5, wherein the artificial neural network is trained with a plurality of images from a plurality of different patients, and wherein the output is used to determine a surgical maneuver of the first segment of the spine of the patient to reduce the difference.

7. The method of claim 5, wherein the output of the artificial neural network comprises a confidence score and the suggested intraoperative motion.

8. A system, comprising:

a processor; and a memory storing data for processing by the processor that, when processed by the processor, cause the processor to:

receive a preoperative image depicting the spine of a patient in a first posture;

receive an intraoperative image depicting the spine of the patient in a second posture while the patient rests on a surgical table in an operating room;

compare the preoperative image of the patient in the first posture with the intraoperative image of the patient in the second posture;

determine, based on comparing the preoperative image of the patient in the first posture with the intraoperative image of the patient in the second posture, a difference between the first posture and the second posture;

determine, based on the difference between the first posture and the second posture, an alignment of a first segment of the spine of the patient with a second segment of the spine of the patient;

provide, via a user interface in the operating room, a suggested intraoperative motion during a surgery or surgical procedure to move the patient on the surgical table from the second posture to a third posture to reduce the difference between the second posture and the first posture, wherein the suggested intraoperative motion is provided before an anatomical element of the patient is surgically manipulated; and update, when the alignment of the first segment with the second segment falls below a threshold value after the patient is moved to the third posture, a planned spinal fusion of the first segment.

9. The system of claim 8, wherein the data further cause the processor to:
provide an indication of the difference;
receive an additional intraoperative image of the patient, wherein the additional intraoperative image of the patient is received after the patient is moved from the second posture to the third posture;
compare the preoperative image of the patient in the first posture with the additional intraoperative image of the patient in the third posture; and
determine, based on comparing the preoperative image of the patient in the first posture with the additional intraoperative image of the patient in the third posture, a difference between the first posture and the third posture.

10. The system of claim 8, wherein the preoperative image of the patient in the first posture comprises a 2D image, and wherein the data further cause the processor to:
generate, based on the 2D image, a 3D model of the anatomical element of the first segment of the spine of the patient; and
compare the 3D model of the anatomical element of the patient with a view of the anatomical element in the intraoperative image.

11. The system of claim 10, wherein the data further cause the processor to:
render, to the user interface, the 3D model of the anatomical element.

12. The system of claim 8, wherein the first posture comprises the patient in a standing position, and wherein the second posture is different from the first posture.

13. The system of claim 12, wherein the second posture comprises the patient in a non-standing position.

14. The system of claim 8, wherein the data further cause the processor to:
cause the preoperative image and the intraoperative image to be provided as an input to an artificial neural network, wherein the artificial neural network provides an output that is used to determine the difference between the first posture and the second posture.

15. The system of claim 14, wherein the artificial neural network is trained with a plurality of images from a plurality of different patients.

16. The system of claim 14, wherein the output of the artificial neural network comprises a confidence score and the suggested intraoperative motion.

17. A system, comprising:
a processor; and
a memory storing data for processing by the processor that, when processed by the processor, cause the processor to:
receive a plurality of preoperative 2D images of the spine of a patient in a first posture;
receive a plurality of intraoperative 2D images of the spine of the patient in a second posture different from the first posture while the patient is resting on a surgical table in an operating room;
generate, based on the plurality of preoperative 2D images, a first 3D model of an anatomical element of the patient in the first posture;
generate, based on the plurality of intraoperative 2D images, a second 3D model of the anatomical element of the patient in the second posture;
compare the first 3D model and the second 3D model;
determine, based on the comparison of the first 3D model and the second 3D model, a difference in a first pose of the anatomical element in the first posture and a second pose of the anatomical element in the second posture;
determine, based on the difference between the first pose and the second pose, an alignment of the anatomical element with a second anatomical element;
provide, via a user interface in the operating room, a suggested intraoperative motion during a surgery or surgical procedure to move the patient on the surgical table from the second pose to a third posture to reduce the difference between the second posture and the first pose, wherein the suggested intraoperative motion is provided before the anatomical element of the patient is surgically manipulated; and
update, when the alignment of the anatomical element with the second anatomical element falls below a threshold value after the patient is moved to the third posture, a planned spinal fusion of the anatomical element with the second anatomical element.

18. The system of claim 17, wherein the data further cause the processor to:
render, to the user interface, the first 3D model and the second 3D model.

* * * * *

UNITED STATES PATENT AND TRADEMARK OFFICE
CERTIFICATE OF CORRECTION

PATENT NO. : 12,133,690 B2  
APPLICATION NO. : 17/497586  
DATED : November 5, 2024  
INVENTOR(S) : Saba Pasha Page 1 of 1

It is certified that error appears in the above-identified patent and that said Letters Patent is hereby corrected as shown below:

In the Claims

In Claim 17, Column 30, Line 33, delete "table from the second pose to a third posture", and insert --table from the second posture to a third posture-- therefor.

In Claim 17, Column 30, Line 34, delete "the difference between the second posture", and insert --the difference between the second pose-- therefor.

Signed and Sealed this  
Twenty-fifth Day of February, 2025

Coke Morgan Stewart  
*Acting Director of the United States Patent and Trademark Office*